(12) United States Patent
Prajapati

(10) Patent No.: US 8,771,319 B2
(45) Date of Patent: Jul. 8, 2014

(54) ROD TO ROD CROSS CONNECTOR

(75) Inventor: Mohit Prajapati, Blue Bell, PA (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 23 days.

(21) Appl. No.: 13/447,608

(22) Filed: Apr. 16, 2012

(65) Prior Publication Data

US 2013/0274807 A1 Oct. 17, 2013

(51) Int. Cl.
*A61B 17/70* (2006.01)
(52) U.S. Cl.
USPC ............................. 606/278; 606/250; 606/251
(58) Field of Classification Search
USPC ............................. 606/250–253, 260, 578, 278
See application file for complete search history.

(56) References Cited

U.S. PATENT DOCUMENTS

| | | | |
|---|---|---|---|
| 3,865,105 A | 2/1975 | Lode | |
| 4,349,017 A | 9/1982 | Sayegh | |
| 4,361,144 A | 11/1982 | Slatis | |
| 4,483,334 A | 11/1984 | Murray | |
| 4,648,388 A | 3/1987 | Steffee | |
| 4,719,905 A | 1/1988 | Steffee | |
| 4,747,400 A | 5/1988 | Koeneman | |
| 4,768,524 A | 9/1988 | Hardy | |
| 4,794,918 A | 1/1989 | Wolter | |
| 4,944,743 A | 7/1990 | Gotzen | |
| 5,002,542 A | 3/1991 | Frigg | |
| 5,005,562 A | 4/1991 | Cotrel | |
| 5,030,220 A | 7/1991 | Howland | |
| 5,053,034 A | 10/1991 | Olerud | |
| 5,074,864 A | 12/1991 | Cozad | |
| 5,084,048 A | 1/1992 | Jacob | |
| 5,084,049 A | 1/1992 | Asher | |
| 5,098,432 A | 3/1992 | Wagenknecht | |
| 5,102,412 A | 4/1992 | Rogozinski | |
| 5,112,332 A | 5/1992 | Cozad | |
| 5,116,334 A | 5/1992 | Cozad | |
| 5,147,359 A | 9/1992 | Cozad | |
| 5,154,718 A | 10/1992 | Cozad | |
| 5,176,678 A | 1/1993 | Tsou | |
| 5,181,917 A | 1/1993 | Rogozinski | |

(Continued)

FOREIGN PATENT DOCUMENTS

| | | |
|---|---|---|
| DE | 3924050 A1 | 1/1991 |
| DE | 29808593 U1 | 10/1999 |

(Continued)

OTHER PUBLICATIONS

Office Action issued in U.S. Appl. No. 13/447,617; notification date Oct. 23, 2013.

*Primary Examiner* — Mary Hoffman
*Assistant Examiner* — Christina Negrellirodrigue
(74) *Attorney, Agent, or Firm* — RatnerPrestia

(57) ABSTRACT

A rod to rod connector includes at least one clamping assembly for receiving a first spinal rod. The clamping assembly may include a polyaxial articulation element. The articulation element may include a hollow body forming an opening. The clamping body may further include a pivot element configured to clamp the first spinal rod between the pivot element and a channel wall in the clamping assembly. The rod to rod connector may also include a connector member for connecting the clamping assembly to a second spinal rod. The connector member may include a socket configured to receive the polyaxial articulation element of the clamping assembly, with the articulation element polyaxially rotatable relative to the axis of the socket.

46 Claims, 4 Drawing Sheets

(56) References Cited

U.S. PATENT DOCUMENTS

| | | |
|---|---|---|
| 5,196,013 A | 3/1993 | Harms |
| 5,201,374 A | 4/1993 | Rahm |
| 5,207,678 A | 5/1993 | Harms |
| 5,254,118 A | 10/1993 | Mirkovic |
| 5,257,993 A | 11/1993 | Asher |
| 5,261,907 A | 11/1993 | Vignaud |
| 5,261,913 A | 11/1993 | Marnay |
| 5,275,600 A | 1/1994 | Allard |
| 5,304,179 A | 4/1994 | Wagner |
| 5,306,275 A | 4/1994 | Bryan |
| 5,312,405 A | 5/1994 | Korotko |
| 5,330,473 A | 7/1994 | Howland |
| 5,334,203 A | 8/1994 | Wagner |
| 5,352,224 A | 10/1994 | Westermann |
| 5,374,267 A | 12/1994 | Siegal |
| 5,380,325 A | 1/1995 | Lahille |
| 5,382,248 A | 1/1995 | Jacobson |
| 5,395,370 A | 3/1995 | Muller |
| 5,397,363 A | 3/1995 | Gelbard |
| 5,403,316 A | 4/1995 | Ashman |
| 5,413,602 A | 5/1995 | Metz-Stavenhagen |
| 5,437,669 A | 8/1995 | Yuan |
| 5,468,241 A | 11/1995 | Metz-Stavenhagen |
| 5,470,333 A | 11/1995 | Ray |
| 5,474,555 A | 12/1995 | Puno |
| 5,476,464 A | 12/1995 | Metz-Stavenhagen |
| 5,487,742 A | 1/1996 | Cotrel |
| 5,498,263 A | 3/1996 | DiNello |
| 5,507,745 A | 4/1996 | Logroscino |
| 5,507,746 A | 4/1996 | Lin |
| 5,514,132 A | 5/1996 | Csernatony |
| 5,522,816 A | 6/1996 | Dinello |
| 5,527,314 A | 6/1996 | Brumfield |
| 5,531,745 A | 7/1996 | Ray |
| 5,531,747 A | 7/1996 | Ray |
| 5,534,002 A | 7/1996 | Brumfield |
| 5,536,268 A | 7/1996 | Griss |
| 5,545,164 A | 8/1996 | Howland |
| 5,545,166 A | 8/1996 | Howland |
| 5,545,167 A | 8/1996 | Lin |
| 5,549,607 A | 8/1996 | Olson |
| 5,562,660 A | 10/1996 | Grob |
| 5,562,662 A | 10/1996 | Brumfield |
| 5,562,663 A | 10/1996 | Wisnewski |
| 5,569,246 A | 10/1996 | Ojima |
| 5,569,247 A | 10/1996 | Morrison |
| 5,601,552 A | 2/1997 | Cotrel |
| 5,609,594 A | 3/1997 | Errico |
| 5,609,992 A | 3/1997 | Sorori |
| 5,611,800 A | 3/1997 | Davis |
| 5,613,968 A | 3/1997 | Lin |
| 5,620,444 A | 4/1997 | Assaker |
| 5,624,442 A | 4/1997 | Mellinger |
| 5,630,816 A | 5/1997 | Kambin |
| 5,643,259 A | 7/1997 | Sasso |
| 5,651,789 A | 7/1997 | Cotrel |
| 5,653,708 A | 8/1997 | Howland |
| 5,667,506 A | 9/1997 | Sutterlin |
| 5,667,507 A | 9/1997 | Corin |
| 5,669,910 A | 9/1997 | Korhonen |
| 5,672,176 A | 9/1997 | Biedermann |
| 5,676,665 A | 10/1997 | Bryan |
| 5,676,703 A | 10/1997 | Gelbard |
| 5,683,393 A | 11/1997 | Ralph |
| 5,688,272 A | 11/1997 | Montague |
| 5,688,275 A | 11/1997 | Koros |
| 5,702,452 A | 12/1997 | Argenson |
| 5,707,372 A | 1/1998 | Errico |
| 5,709,684 A | 1/1998 | Errico |
| 5,709,685 A | 1/1998 | Dombrowski |
| 5,716,355 A | 2/1998 | Jackson |
| 5,716,356 A | 2/1998 | Biedermann |
| 5,727,899 A | 3/1998 | Dobrovolny |
| 5,733,285 A | 3/1998 | Errico |
| 5,733,286 A | 3/1998 | Errico |
| 5,735,850 A | 4/1998 | Baumgartner |
| 5,735,851 A | 4/1998 | Errico |
| 5,735,853 A | 4/1998 | Olerud |
| 5,741,254 A | 4/1998 | Henry |
| 5,741,255 A | 4/1998 | Krag |
| 5,743,911 A | 4/1998 | Cotrel |
| 5,746,741 A | 5/1998 | Kraus |
| 5,752,955 A | 5/1998 | Errico |
| 5,800,548 A | 9/1998 | Martin |
| 5,810,816 A | 9/1998 | Roussouly |
| 5,814,046 A | 9/1998 | Hopf |
| 5,876,403 A | 3/1999 | Shitoto |
| 5,885,284 A | 3/1999 | Errico |
| 5,899,903 A | 5/1999 | Cotrel |
| 5,928,231 A | 7/1999 | Klein |
| 5,938,663 A | 8/1999 | Petreto |
| 5,947,965 A | 9/1999 | Bryan |
| 5,947,966 A | 9/1999 | Drewry |
| 5,947,967 A | 9/1999 | Barker |
| 5,976,133 A | 11/1999 | Kraus |
| 5,976,135 A | 11/1999 | Sherman |
| 5,980,521 A | 11/1999 | Montague |
| 5,980,523 A | 11/1999 | Jackson |
| 5,984,922 A | 11/1999 | McKay |
| 5,984,923 A | 11/1999 | Breard |
| 5,984,924 A | 11/1999 | Asher |
| 5,989,250 A | 11/1999 | Wagner |
| 5,989,251 A | 11/1999 | Nichols |
| 5,997,539 A | 12/1999 | Errico |
| 6,027,533 A | 2/2000 | Olerud |
| 6,030,388 A | 2/2000 | Yoshimi |
| 6,050,997 A | 4/2000 | Mullane |
| 6,063,090 A | 5/2000 | Schlapfer |
| 6,077,262 A | 6/2000 | Schlapfer |
| 6,080,156 A | 6/2000 | Asher |
| 6,083,226 A | 7/2000 | Fiz |
| 6,090,110 A | 7/2000 | Metz-Stavenhagen |
| 6,096,039 A | 8/2000 | Stoltenberg |
| 6,110,173 A | 8/2000 | Thomas |
| 6,113,600 A | 9/2000 | Drummond |
| 6,113,601 A | 9/2000 | Tatar |
| 6,132,430 A | 10/2000 | Wagner |
| 6,136,003 A | 10/2000 | Hoeck |
| 6,139,548 A | 10/2000 | Errico |
| 6,171,311 B1 | 1/2001 | Richelsoph |
| 6,176,861 B1 | 1/2001 | Bernstein |
| 6,179,838 B1 | 1/2001 | Fiz |
| 6,179,841 B1 | 1/2001 | Jackson |
| 6,183,473 B1 | 2/2001 | Ashman |
| 6,187,005 B1 | 2/2001 | Brace |
| 6,210,413 B1 | 4/2001 | Justis |
| 6,214,006 B1 | 4/2001 | Metz-Stavenhagen |
| 6,217,578 B1 | 4/2001 | Crozet |
| 6,231,575 B1 | 5/2001 | Krag |
| 6,234,705 B1 | 5/2001 | Troxell |
| 6,238,396 B1 | 5/2001 | Lombardo |
| 6,254,602 B1 | 7/2001 | Justis |
| 6,254,603 B1 | 7/2001 | Gertzbein |
| 6,258,090 B1 | 7/2001 | Jackson |
| 6,261,287 B1 | 7/2001 | Metz-Stavenhagen |
| 6,264,658 B1 | 7/2001 | Lee |
| 6,267,765 B1 | 7/2001 | Taylor |
| 6,273,888 B1 | 8/2001 | Justis |
| 6,280,442 B1 | 8/2001 | Barker |
| 6,280,443 B1 | 8/2001 | Gu |
| 6,280,445 B1 | 8/2001 | Morrison |
| 6,283,967 B1 | 9/2001 | Troxell |
| 6,287,308 B1 | 9/2001 | Betz |
| 6,287,309 B1 | 9/2001 | Baccelli |
| 6,287,311 B1 | 9/2001 | Sherman |
| 6,290,700 B1 | 9/2001 | Schmotzer |
| 6,290,703 B1 | 9/2001 | Ganem |
| 6,299,614 B1 | 10/2001 | Kretschmer |
| 6,302,882 B1 | 10/2001 | Lin |
| 6,302,888 B1 | 10/2001 | Mellinger |
| 6,306,137 B2 | 10/2001 | Troxell |
| 6,309,135 B1 | 10/2001 | Thomson |
| 6,309,390 B1 | 10/2001 | Le Couedic |
| 6,309,391 B1 | 10/2001 | Crandall |

(56) References Cited

U.S. PATENT DOCUMENTS

| | | |
|---|---|---|
| 6,326,740 B1 | 12/2001 | Chang |
| 6,328,740 B1 | 12/2001 | Richelsoph |
| 6,328,741 B1 | 12/2001 | Richelsoph |
| 6,361,535 B2 | 3/2002 | Jackson |
| 6,368,319 B1 | 4/2002 | Schaefer |
| 6,368,321 B1 | 4/2002 | Jackson |
| 6,371,957 B1 | 4/2002 | Amrein |
| 6,375,657 B1 | 4/2002 | Doubler |
| 6,379,354 B1 | 4/2002 | Rogozinski |
| 6,379,357 B1 | 4/2002 | Bernstein |
| 6,402,751 B1 | 6/2002 | Hoeck |
| 6,443,953 B1 | 9/2002 | Perra |
| 6,458,132 B2 | 10/2002 | Choi |
| 6,471,705 B1 | 10/2002 | Biedermann |
| 6,524,310 B1 | 2/2003 | Lombardo |
| 6,537,276 B2 | 3/2003 | Metz-Stavenhagen |
| 6,554,832 B2 | 4/2003 | Shluzas |
| 6,565,568 B1 | 5/2003 | Rogozinski |
| 6,565,569 B1 | 5/2003 | Assaker |
| 6,569,164 B1 | 5/2003 | Assaker |
| 6,572,618 B1 | 6/2003 | Morrison |
| 6,574,789 B1 | 6/2003 | Yamauchi |
| 6,602,253 B2 | 8/2003 | Richelsoph |
| 6,610,063 B2 | 8/2003 | Kumar |
| 6,616,668 B2 | 9/2003 | Altarac |
| 6,618,960 B2 | 9/2003 | Brown |
| 6,620,164 B2 | 9/2003 | Ueyama |
| 6,626,908 B2 | 9/2003 | Cooper |
| 6,652,535 B2 | 11/2003 | Kvarnstrom |
| 6,673,073 B1 | 1/2004 | Schäfer |
| 6,685,705 B1 | 2/2004 | Taylor |
| 6,699,248 B2 | 3/2004 | Jackson |
| 6,736,816 B2 | 5/2004 | Ritland |
| 6,736,817 B2 | 5/2004 | Troxell |
| 6,736,820 B2 | 5/2004 | Biedermann |
| 6,740,086 B2 | 5/2004 | Richelsoph |
| 6,749,361 B2 | 6/2004 | Hermann |
| 6,749,612 B1 | 6/2004 | Conchy |
| 6,749,613 B1 | 6/2004 | Conchy |
| 6,758,545 B2 | 7/2004 | Ikeda |
| 6,770,075 B2 | 8/2004 | Howland |
| 6,773,214 B2 | 8/2004 | Jakubowski |
| 6,783,526 B1 | 8/2004 | Lin |
| 6,786,907 B2 | 9/2004 | Lange |
| 6,872,208 B1 | 3/2005 | McBride |
| 6,872,209 B2 | 3/2005 | Morrison |
| 6,875,211 B2 | 4/2005 | Nichols |
| 6,887,241 B1 | 5/2005 | McBride |
| 6,960,212 B2 | 11/2005 | Richelsoph et al. |
| 6,964,665 B2 | 11/2005 | Thomas |
| 7,008,423 B2 | 3/2006 | Assaker |
| 7,033,358 B2 | 4/2006 | Taylor |
| 7,081,116 B1 | 7/2006 | Carly |
| 7,112,036 B2 | 9/2006 | Lubell |
| 7,122,036 B2 | 10/2006 | Vanacker |
| 7,128,743 B2 | 10/2006 | Metz-Stavenhagen |
| 7,137,986 B2 | 11/2006 | Troxell |
| 7,166,108 B2 | 1/2007 | Mazda |
| 7,270,665 B2 | 9/2007 | Morrison |
| 7,314,467 B2 | 1/2008 | Howland |
| 7,322,979 B2 | 1/2008 | Crandall |
| 7,717,938 B2 | 5/2010 | Kim |
| 7,744,632 B2 | 6/2010 | Usher |
| 8,246,657 B1 | 8/2012 | Samuel |
| 2002/0035366 A1 | 3/2002 | Walder |
| 2002/0143327 A1 | 10/2002 | Shluzas |
| 2003/0004512 A1 | 1/2003 | Farris |
| 2003/0060823 A1 | 3/2003 | Bryan |
| 2003/0114853 A1 | 6/2003 | Burgess |
| 2004/0044344 A1 | 3/2004 | Winquist |
| 2004/0092930 A1 | 5/2004 | Petit |
| 2004/0116928 A1 | 6/2004 | Young |
| 2004/0133202 A1 | 7/2004 | Suzuki |
| 2004/0133203 A1 | 7/2004 | Young |
| 2004/0260285 A1 | 12/2004 | Steib |
| 2005/0080416 A1 | 4/2005 | Ryan |
| 2005/0080419 A1 | 4/2005 | Donath |
| 2005/0090821 A1 | 4/2005 | Berrevoets |
| 2005/0107789 A1 | 5/2005 | Sweeney |
| 2005/0228377 A1 | 10/2005 | Chao |
| 2006/0058789 A1 | 3/2006 | Kim |
| 2006/0064093 A1 | 3/2006 | Thramann |
| 2006/0084996 A1 | 4/2006 | Metz-Stavenhagen |
| 2006/0206114 A1 | 9/2006 | Ensign |
| 2006/0217712 A1 | 9/2006 | Mueller |
| 2006/0233597 A1 | 10/2006 | Ensign |
| 2006/0247622 A1 | 11/2006 | Maughan |
| 2006/0271051 A1 | 11/2006 | Berrevoets |
| 2007/0049932 A1 | 3/2007 | Richelsoph |
| 2008/0177315 A1* | 7/2008 | Usher .......................... 606/253 |
| 2012/0226316 A1* | 9/2012 | Dant et al. .................. 606/250 |

FOREIGN PATENT DOCUMENTS

| | | |
|---|---|---|
| EP | 0536066 A1 | 4/1993 |
| EP | 0596788 A1 | 5/1994 |
| EP | 0734688 A2 | 10/1996 |
| EP | 0793947 A1 | 9/1997 |
| EP | 0836836 A2 | 4/1998 |
| EP | 0878170 A2 | 11/1998 |
| EP | 0956829 A2 | 11/1999 |
| EP | 1093761 A2 | 4/2001 |
| EP | 1103226 A2 | 5/2001 |
| EP | 0746255 B1 | 9/2002 |
| FR | 2697742 A1 | 5/1994 |
| FR | 2781359 A1 | 1/2000 |
| FR | 2804314 A1 | 8/2001 |
| WO | WO-9101115 A1 | 2/1991 |
| WO | WO-9106254 A1 | 5/1991 |
| WO | WO-9311715 A1 | 6/1993 |
| WO | WO-9321847 A1 | 11/1993 |
| WO | WO-9400062 A1 | 1/1994 |
| WO | WO-9400066 A1 | 1/1994 |
| WO | WO-9406361 A2 | 3/1994 |
| WO | WO-9408530 A1 | 4/1994 |
| WO | WO-9414384 A2 | 7/1994 |
| WO | WO-9420048 A1 | 9/1994 |
| WO | WO-9502372 A2 | 1/1995 |
| WO | WO-9508298 A1 | 3/1995 |
| WO | WO-9513753 A1 | 5/1995 |
| WO | WO-9513754 A1 | 5/1995 |
| WO | WO-9513755 A1 | 5/1995 |
| WO | WO-9513756 A1 | 5/1995 |
| WO | WO-9525473 A1 | 9/1995 |
| WO | WO-9526687 A1 | 10/1995 |
| WO | WO-9528889 A1 | 11/1995 |
| WO | WO-9531147 A1 | 11/1995 |
| WO | WO-9535067 A2 | 12/1995 |
| WO | WO-9602200 A1 | 2/1996 |
| WO | WO-9628106 A1 | 9/1996 |
| WO | WO-9632070 A2 | 10/1996 |
| WO | WO-9636291 A1 | 11/1996 |
| WO | WO-9639090 A1 | 12/1996 |
| WO | WO-9639972 A1 | 12/1996 |
| WO | WO 9641582 A1 | 12/1996 |
| WO | WO-9706742 A1 | 2/1997 |
| WO | WO-9714368 A1 | 4/1997 |
| WO | WO-9723170 A1 | 7/1997 |
| WO | WO-9731579 A1 | 9/1997 |
| WO | WO-9731580 A1 | 9/1997 |
| WO | WO-9738640 A1 | 10/1997 |
| WO | WO-9743974 A1 | 11/1997 |
| WO | WO-9815233 A1 | 4/1998 |
| WO | WO-9817188 A1 | 4/1998 |
| WO | WO-9837824 A1 | 9/1998 |
| WO | WO-9843551 A1 | 10/1998 |
| WO | WO-9855038 A1 | 12/1998 |
| WO | WO-9900065 A1 | 1/1999 |
| WO | WO-9903415 A1 | 1/1999 |
| WO | WO-9909901 A1 | 3/1999 |
| WO | WO-9915094 A1 | 4/1999 |
| WO | WO-9918874 A1 | 4/1999 |
| WO | WO-9929248 A1 | 6/1999 |
| WO | WO-9949802 A1 | 10/1999 |

(56) References Cited

FOREIGN PATENT DOCUMENTS

| | | |
|---|---|---|
| WO | WO-9955246 A1 | 11/1999 |
| WO | WO-9955247 A1 | 11/1999 |
| WO | WO-9956652 A1 | 11/1999 |
| WO | WO-0006038 A1 | 2/2000 |
| WO | WO-0015125 A1 | 3/2000 |
| WO | WO-0015126 A1 | 3/2000 |
| WO | WO-0016710 A1 | 3/2000 |
| WO | WO-0021447 A1 | 4/2000 |
| WO | WO-0021477 A1 | 4/2000 |
| WO | WO-0025689 A1 | 5/2000 |
| WO | WO-0042930 A1 | 7/2000 |
| WO | WO-0048523 A1 | 8/2000 |
| WO | WO-0054681 A2 | 9/2000 |
| WO | WO-0057801 A1 | 10/2000 |
| WO | WO-0059387 A1 | 10/2000 |
| WO | WO-0062691 A1 | 10/2000 |
| WO | WO-0062692 A2 | 10/2000 |
| WO | WO-0072769 A1 | 12/2000 |
| WO | WO-0072770 A1 | 12/2000 |
| WO | WO-0076413 A1 | 12/2000 |
| WO | WO-0101872 A1 | 1/2001 |
| WO | WO-0101873 A1 | 1/2001 |
| WO | WO-0106939 A1 | 2/2001 |
| WO | WO-0106940 A1 | 2/2001 |
| WO | WO-0108574 A1 | 2/2001 |
| WO | WO-0110317 A1 | 2/2001 |
| WO | WO-0115612 A1 | 3/2001 |
| WO | WO-0119266 A1 | 3/2001 |
| WO | WO-0124718 A1 | 4/2001 |
| WO | WO-0139677 A1 | 6/2001 |
| WO | WO-0152756 A1 | 7/2001 |
| WO | WO-0152757 A1 | 7/2001 |
| WO | WO-0152758 A1 | 7/2001 |
| WO | WO-0154597 A1 | 8/2001 |
| WO | WO-0158369 A1 | 8/2001 |
| WO | WO-0167972 A2 | 9/2001 |
| WO | WO-0167973 A2 | 9/2001 |
| WO | WO-0178613 A1 | 10/2001 |
| WO | WO-0191656 A2 | 12/2001 |
| WO | WO-0200124 A1 | 1/2002 |
| WO | WO-0200125 A1 | 1/2002 |
| WO | WO-0200126 A1 | 1/2002 |
| WO | WO-0202024 A1 | 1/2002 |
| WO | WO-0209603 A1 | 2/2002 |
| WO | WO-0215766 A2 | 2/2002 |
| WO | WO-0230307 A2 | 4/2002 |
| WO | WO-0234149 A2 | 5/2002 |
| WO | WO-0234151 A2 | 5/2002 |
| WO | WO-0238060 A1 | 5/2002 |
| WO | WO-0238061 A1 | 5/2002 |
| WO | WO-0238063 A2 | 5/2002 |
| WO | WO-0241797 A1 | 5/2002 |
| WO | WO-0245606 A1 | 6/2002 |
| WO | WO-0245607 A1 | 6/2002 |
| WO | WO-02078517 A2 | 10/2002 |
| WO | WO-02091931 A1 | 11/2002 |
| WO | WO-03037198 A1 | 5/2003 |
| WO | WO-03068087 A1 | 8/2003 |
| WO | WO-03099148 A2 | 12/2003 |
| WO | WO-2004010881 A1 | 2/2004 |
| WO | WO-2004021902 A1 | 3/2004 |
| WO | WO-2004039268 A1 | 5/2004 |
| WO | WO-2004039269 A2 | 5/2004 |
| WO | WO-2004096065 A1 | 11/2004 |
| WO | WO-2004110289 A1 | 12/2004 |
| WO | WO-2004112626 A2 | 12/2004 |

* cited by examiner

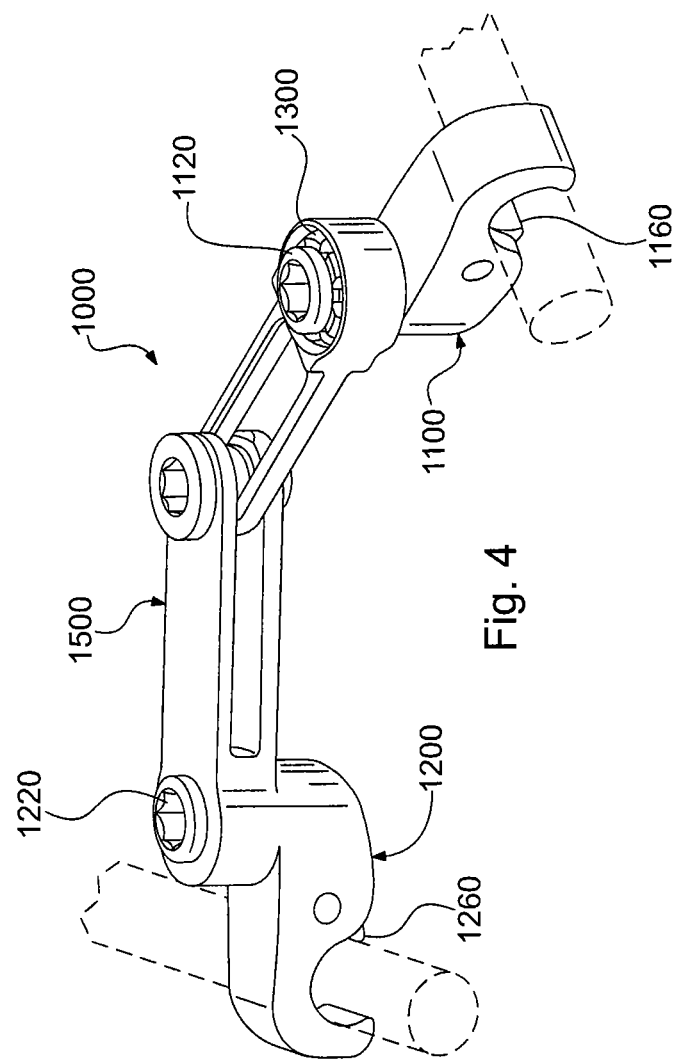

ROD TO ROD CROSS CONNECTOR

FIELD

The present invention relates generally to systems for stabilization and fixation the spine, and more particularly to an assembly for rigidly connecting two spinal rods together, with mechanisms that allow for the connection of two non-parallel rods that extend in different planes.

BACKGROUND

Spinal rods are often used for spinal fixation, including for correction of scoliotic curves. Fixation often involves implantation of rods by attaching them to the spine with anchors in the form of hooks and/or pedicle screws. Often, a pair of rods are placed on opposite sides of the spine.

Various systems have been developed for rigidly connecting two spinal rods together to prevent rod migration and to increase stiffness of the paired rod assembly. In many cases involving multi-level fusion of the spine, these systems stabilize the spine construct until solid bone fusion is accomplished. In the post-operative period before fusion occurs, a significant amount of motion can occur between the rods, wires and hooks, which can, for example, allow a scoliotic correlation to decrease or the pelvis to de-rotate toward its previous, deformed position. By providing a rigid transverse connection between two spinal rods, the loss of correction can be reduced and a stiffer construct can be created, which may enhance the promotion of solid fusion.

In some cases, the two side-by-side spinal rods that are to be interconnected by a rod to rod connector are not perfectly parallel to each other. In addition, the spinal rods may extend in different planes. Non-parallel rods that extend in different planes present a problem because many known rod connectors require the two spinal rods to be more or less parallel and co-planar. Many known rod to rod connectors cannot engage rods that extend in different planes. Longer rod pairs that span two or more levels can be especially difficult to interconnect, because the different planar orientations are more pronounced.

SUMMARY

The drawbacks and limitations of known rod to rod connectors are addressed in many respects by rod to rod connectors in accordance with the invention. Rod to rod connectors in accordance with the invention may include one or more polyaxial clamping assemblies that can align with different rod orientations in different planes. For example, a rod to rod connector may include at least one clamping assembly having a clamping body with a channel defined by a channel wall for receiving a first spinal rod. A bore may extend through the clamping body. The clamping assembly may feature a polyaxial articulation element. The articulation element may include a hollow body forming an opening, the opening being adjacent to the bore that extends through the clamping body. The clamping body may further include a pivot element pivotally connected to the clamping body. The pivot element may be configured to clamp a spinal rod between the pivot element and the channel wall in the clamping assembly. The rod to rod connector may also feature a connector member for connecting the clamping assembly to a second spinal rod. The connector member may include a socket having an axis. The socket may be configured to receive the articulation element of the clamping assembly, with the articulation element polyaxially rotatable relative to the axis of the socket.

BRIEF DESCRIPTION OF THE DRAWINGS

The foregoing summary and the following detailed description will be better understood in conjunction with the drawing figures, of which:

FIG. 4 is a perspective view of a rod to rod connector in accordance with a second exemplary embodiment.

DETAILED DESCRIPTION OF PREFERRED EMBODIMENTS

Figure 1:
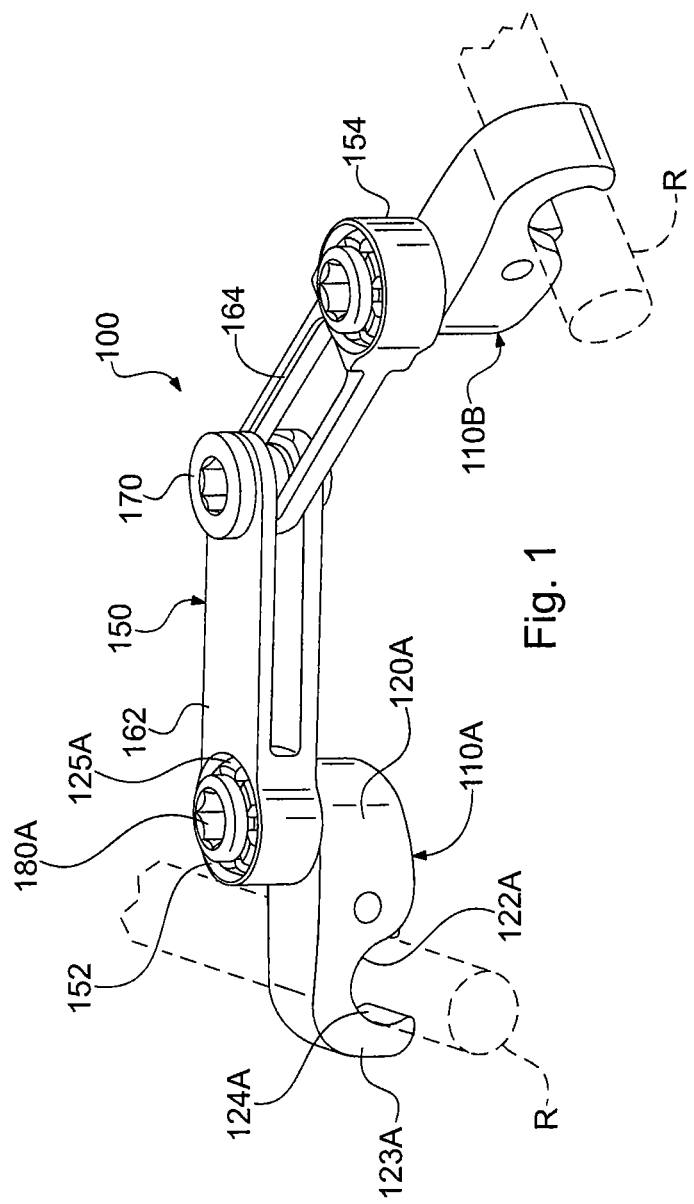
FIG. 1 is a perspective view of a rod to rod connector in accordance with a first exemplary embodiment, the rod to rod connector shown in a first configuration.

Although the invention is illustrated and described herein with reference to specific embodiments, the invention is not intended to be limited to the details shown. Rather, various modifications may be made in the details within the scope and range of equivalents of the claims and without departing from the invention.

In one embodiment, a rod to rod connector may include a clamping assembly having a clamping body with a channel defined by a channel wall for receiving a first spinal rod. A bore extends through the clamping body. The clamping assembly may also feature a polyaxial articulation element. The articulation element may include a hollow body forming an opening, the opening being adjacent to the bore that extends through the clamping body. The clamping body may further include a pivot element pivotally connected to the clamping body. The pivot element may be configured to clamp the first spinal rod between the pivot element and the channel wall in the clamping assembly. The rod to rod connector may also feature a connector member for connecting the clamping assembly to a second spinal rod. The connector member may include a socket having an axis. The socket may be configured to receive the articulation element of the clamping assembly, with the articulation element polyaxially rotatable relative to the axis of the socket.

The connector member may include a first connector member section and a second connector member section configured to be pivotally coupled with the first connector member section. The first connector member section may feature a plate forming a first slot, and the second connector member section may feature a plate forming a second slot. A connector element may extend through the first and second slots and pivotally connect the first and second connector member sections.

The rod to rod connector may also include a fastener extending through the socket in the connector member, and through the opening and bore in the clamping assembly. The fastener may interconnect the connector member and clamping assembly.

The articulation element of the clamping assembly may include a plurality of wall sections separated from one another by slits. Each wall section may be displaceable between a first position, in which each wall section is in a relaxed state, and a second position, in which each wall section is displaced radially outwardly from the first position. The fastener may be drivable into the opening of the clamping assembly to displace each wall section of the articulation element from the first position to the second position. This displacement provides a locking function, as described below in more detail.

The pivot element of the clamping assembly may include a clamping end and a pivot end. The pivot end may be aligned with the bore in the clamping assembly and positioned to be engaged by the fastener when the fastener is driven through the opening of the clamping assembly.

The fastener may be operable to perform a first locking function. In the first locking function, the fastener locks the connector member relative to the articulation element. The fastener may also be operable to perform a second locking function. In the second locking function, the fastener locks a spinal rod in the channel of the clamping assembly. The fastener may be operable to perform the first and second locking functions during a single act of rotating the fastener, and may be operable, depending on the configuration, to execute the first and second locking functions simultaneously.

The rod to rod connector may include first and second clamping assemblies. Each clamping assembly may include the same clamping assembly features described above. The first clamping assembly may include a clamping body having a channel defined by a channel wall for receiving a first spinal rod, and a bore extending through the clamping body. The first clamping assembly may also include a polyaxial articulation element. The articulation element may include a hollow body and an opening, the opening being adjacent to the bore extending through the clamping body. The first clamping assembly may further include a pivot element pivotally connected to the clamping body. The pivot element may be configured to clamp a first spinal rod between the pivot element and the channel wall in the first clamping assembly.

The second clamping assembly may include a clamping body having a channel defined by a channel wall for receiving a second spinal rod, and a bore extending through the clamping body. The second clamping assembly may also include a polyaxial articulation element. The articulation element may include a hollow body and an opening, the opening being adjacent to the bore extending through the clamping body. The second clamping assembly may further include a pivot element pivotally connected to the clamping body. The pivot element may be configured to clamp a second spinal rod between the pivot element and the channel wall in the second clamping assembly.

The rod to rod connector may include a connector member for connecting the first clamping assembly with the second clamping assembly. The connector member may have the same connector member features described above, including a first socket having a first axis, and a second socket having a second axis. The first socket may be configured to receive the articulation element of the first clamping assembly, and the second socket may be configured to receive the articulation element of the second clamping assembly. The articulation elements of the first and second clamping assemblies may be polyaxially rotatable relative to the first and second axes of the corresponding sockets.

Figure 2:
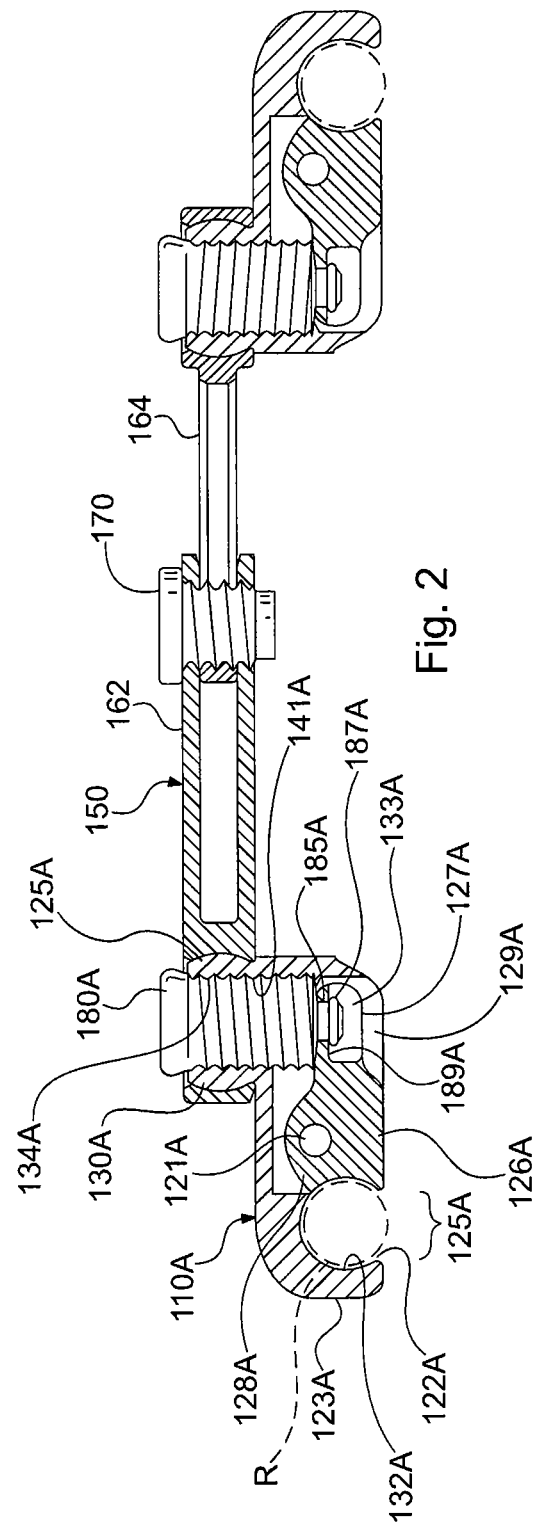
FIG. 2 is a front cross section view of the rod to rod connector of FIG. 1, shown in a second configuration.
Figure 3:
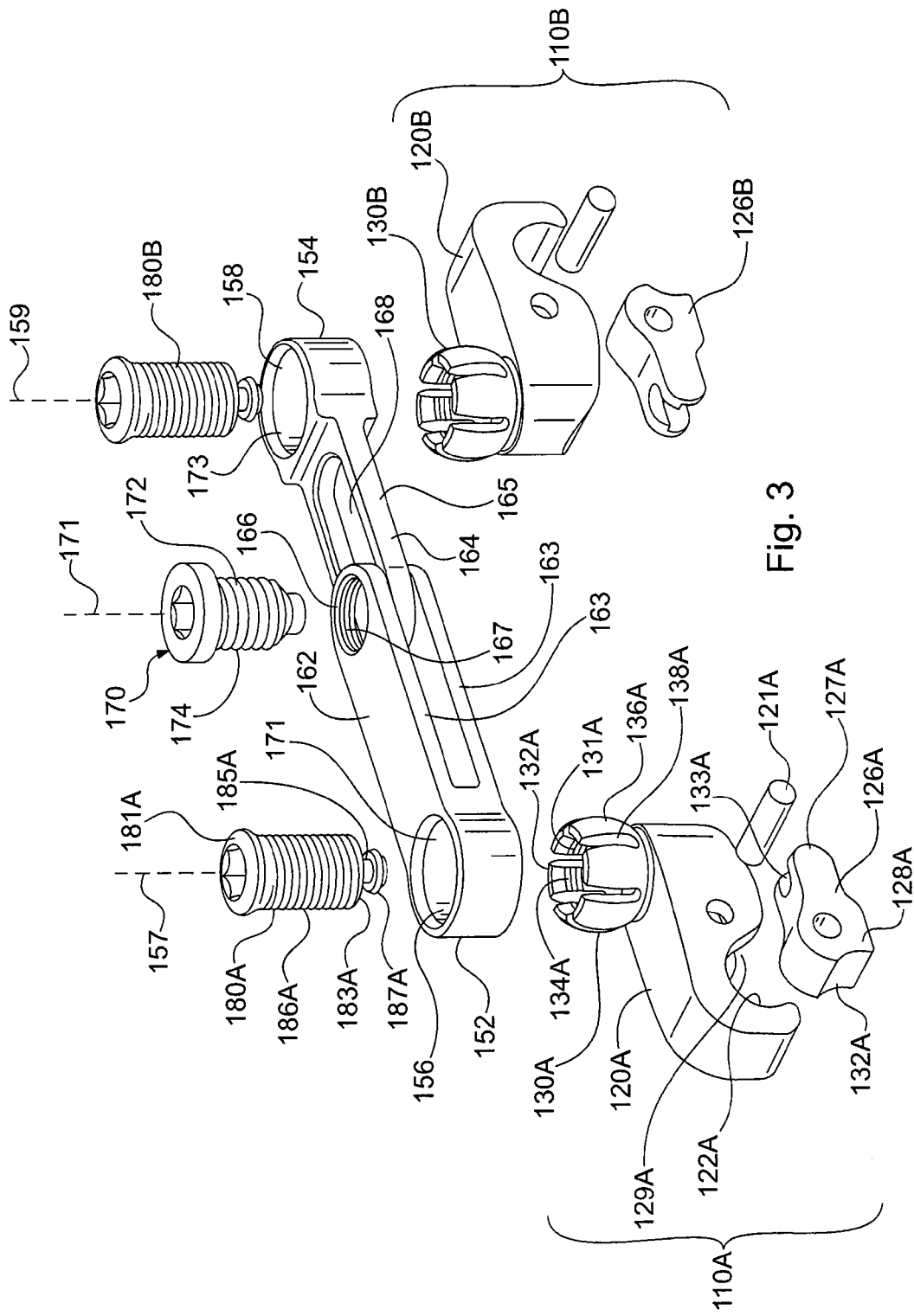
FIG. 3 is an exploded perspective view of the rod to rod connector of FIG. 1.

Referring to FIGS. 1-3, a rod to rod connector assembly 100 is shown in accordance with one exemplary embodiment. Assembly 100 can be used to interconnect two spinal fixation rods and form a bridge or cross link that enhances the stability of the two rods. Assembly 100 includes a first clamping assembly 110A, a second clamping assembly 110B, and a connector member 150 that interconnects the first and second clamping assemblies.

Rod to rod connectors in accordance with the invention include at least one clamping assembly that is polyaxially displaceable relative to the connector member. The term "polyaxial", as used in this description, refers to the ability of an element, such as a screw, to rotate about multiple axes relative to another object in which the element is contained. For example, a polyaxial screw that is seated in a screw hole in a plate would be configured to rotate about the longitudinal axis of the screw hole, and other axes that are angularly offset from the axis of the screw hole. As such, the polyaxial screw is configured to tilt as well as rotate relative to the plate. This is in contrast to a "monoaxial" screw, which is configured to rotate about one and only one axis relative to the object in which it is contained; i.e., the screw is maintained on one axis and is not allowed to tilt relative to the plate.

In some applications, it may be desirable to provide both clamping assemblies with the ability to move polyaxially relative to the connector member. Providing both clamping assemblies with the ability to move polyaxially allows for greater flexibility in operation and a larger range of angular adjustment, as will be described below.

In assembly 100, both clamping assemblies 110A and 110B can move polyaxially relative to connector member 150. First clamping assembly 110A is polyaxially displaceable relative to the connector member 150, and second clamping assembly 110B is also polyaxially displaceable relative to the connector member. Moreover, first clamping assembly 110A and second clamping assembly 110B are independently displaceable relative to each other. The ability of each clamping assembly 110A and 110B to move polyaxially and independently allows the clamping assemblies to clamp onto non-parallel rods that extend in different planes.

Clamping assembly 110A and clamping assembly 110B are configured identically, and have identical components. Therefore, only the features of clamping assembly 110A will be described, with the understanding that identical elements are present on clamping assembly 110B. Features of clamping assembly 110A are identified with reference numbers followed by the suffix "A". Some of the corresponding features on clamping assembly 110B are labeled in the drawings with the same reference number followed by the suffix "B".

Clamping assemblies in accordance with the invention may feature a number of components for clamping and releasing spinal rods. Clamping assembly 110A includes a clamping body 120A having a clamping end 123A and an articulating end 125A. Clamping end 123A has a channel 122A defined in part by a channel wall 124A. Channel 122A is generally cylindrical and sized to conform with the cylindrical exterior of a spinal rod R. Clamping assembly 110A also has a pivot element 126A pivotally connected to clamping body 120A. Pivot element 126A is pivotable relative to clamping body 120A to clamp onto or release spinal rod R. Pivot element 126A is pivotally connected to clamping body 120A by a pin 121A. Pivot element 126A has a pivoting end 127A and a clamping end 128A opposite the pivoting end. Pivoting end 127A is mounted on pin 121A and extends inside a hollow interior space 129A of clamping body 120A. Clamping end 128A faces into channel 122A, and includes an arc shaped notch 132A sized and configured to conform to the round exterior of a spinal rod R.

Clamping bodies in accordance with the invention may include a polyaxial articulation element that allows polyaxial rotation of the clamping body with respect to the connecting member. The articulation element may have a variety of geometrical configurations to allow polyaxial rotation of the clamping body about multiple axes, including but not limited to a spherical or elliptical geometry. Clamping body 120A includes a generally spherical articulation element 130A that extends upwardly from articulating end 125A. Articulation element 130A and channel 122A are located on the opposite sides of clamping body 120A. Articulation elements need not be positioned opposite the channel, however, and can be positioned on any side of the clamping body.

Articulation element 130A has a hollow body 132A and an opening 134A. Opening 134A extends through hollow body 132A and aligns with a bore 141A that extends through clamping body 120A. Bore 141A connects with hollow interior space 129A, forming a passage that connects opening 134A with the hollow interior space. Hollow body 132A includes an plurality of wall sections 136A arranged in a circular array around opening 134A. Wall sections 136A are separated from one another by a plurality of slits 138A. Each wall section 136A is displaceable between a first position, in which the wall section is in a relaxed state, and a second position, in which the wall section is splayed radially outwardly from the first position.

Connector member 150 has a first end 152 that connects with first clamping assembly 110A and a second end 154 that connects with second clamping assembly 110B. First end 152 includes a socket 156 for receiving articulation element 130A, and second end 154 includes a socket 158 for receiving articulation element 130B. Socket 156 has a rounded inner surface 171 that generally conforms to the contour of articulation element 130A. Likewise, socket 158 has a rounded inner surface 173 that generally conforms to the contour of articulation element 130B. Socket 156 is characterized by a longitudinal axis 157, and socket 158 is characterized by a longitudinal axis 159. The term "longitudinal axis", when used in connection with the sockets in the connector member, is defined as the straight line axis that passes between the open ends of the socket, which intersects the center points of the openings. The rounded shapes of articulation elements 130A and 130B allow each clamping assembly to rotate polyaxially relative to the connector member 150.

Connector member 150 includes a first connector member section 162 and a second connector member section 164 pivotally coupled with the first connector member section. First connector member section 162 includes a link portion formed of two parallel plates 163 and a first slot 166 extending transversely through the plates. Second connector member section 164 includes a link portion forming a single plate 165 having a second slot 168. In the assembled condition shown, plate 165 is inserted between plates 163, with first slot 166 aligned with second slot 168. A connector element 170 extends through the first and second slots 166 and 168 and pivotally connects the first and second connector member sections 162 and 164.

Connector element 170 has a male thread 172 and first slot 166 has female thread 167 that mates with the male thread. In this arrangement, first slot 166 receives connector element 170 in a threaded engagement. Connector element 170 can be partially threaded into first slot 166 to connect the first and second connector member sections 162 and 164 in a loose connection that allows the first and second connector member sections to move relative to one another. Connector element 170 can also be completely threaded into first slot 166 to connect the first and second connector member sections 162 and 164 in a tightened connection that prevents rotation and fixes the first and second connector member sections relative to one another.

Second slot 168 is an elongated slot that is sized to receive shaft 174 of connector element 170. When connector element 170 is partially threaded into first slot 166, i.e. in the loosened connection, plate 165 on second connector member section 164 can translate relative to plates 163 on first connector member section 162. Translation of plates 163 relative to plate 165 adjusts the spacing between the first and second clamping assemblies 110A and 110B to be adjusted. In addition, the translation of plates 163 relative to plate 165 allows first connector member section 162 to be rotated relative to second connector member section 164. This rotation allows the connector member 150 to be adjusted to a "bent" configuration, as shown in FIG. 1, or adjusted to a linear configuration, as shown in FIG. 2. First and second connector member sections 162 and 164 are configured to rotate about an axis 171 defined by shaft 174 of connector element 170 when the connector element is in the loosened condition.

A first fastener 180A connects first connector member section 162 to fastener assembly 110A. A second fastener 180B connects second connector member section 164 to fastener assembly 110B. First fastener 180A and second fastener 180B are identically configured. Therefore, only the features of first fastener 180A will be described, with the understanding that identical features are present on second fastener 180B. Features of first fastener 180A are identified with reference numbers followed by the suffix "A". Corresponding features on second fastener 180B are labeled in the drawings with the same reference number followed by the suffix "B".

First fastener 180A is a screw featuring a first end 181A and a second end 183A opposite the first end. First end 181A features a ramped head 182A. A shaft 184A extends between first end 181A and second end 183A, and has a male thread 186A. Opening 134A in articulation element 130A has a female thread 131A. First fastener 180A extends through socket 156, opening 134A and bore 141A to interconnect the first connector member section 162 and first clamping assembly 110A. Second end 183A features a reduced diameter section or peg 185A. Peg 185A has a widened section forming a detent 187A. Peg 185A extends through a slot 133A in pivot element 126A, with detent 187A extending inside the slot beneath an undercut 189A. Detent 187A is wider than the shortest dimension or width of slot 133A. In this configuration, detent 187A prevents pivoting end 127A from slipping off peg 185A as peg is moved axially in clamping assembly 110A.

First fastener 180A is drivable into opening 134A of first clamping assembly 110A to provide two separate locking functions. The first locking function locks the first connector member section 162 relative to articulation element 130A. This function is performed by driving first fastener 180A into opening 134A. The diameter of shaft 184A is sufficiently wide to splay wall sections 136A of articulation element 130A outwardly and into the second position. When wall sections 136A are splayed outwardly to the second position, the wall sections bear against and frictionally engage the interior of socket 156, preventing first connector member section 162 from moving relative to articulation member 130A. In this condition, first clamping assembly 110A is locked against further polyaxial movement relative to first connector member section 162.

The second locking function locks the first clamping assembly 110A to a spinal rod. Pivoting end 127A of pivot element 126A is aligned with the bore in first clamping assembly 110A. In this arrangement, pivoting end 127A is positioned to be engaged by first fastener 180A when the first fastener is driven through bore 141A of first clamping assembly 110A. Pivot element 126A is rotatable on pin 121A between a first position, in which pivoting end 127A is "raised" or positioned toward articulation element 130A, and a second position, in which the pivoting end is "lowered" or moved away from the articulation element. When pivoting end 127A is raised, clamping end 128A is lowered so that the arc shaped notch 132A is moved downwardly or away from channel wall 124A. This has the effect of widening the mouth 125A of channel 122A to allow a rod to enter or exit the channel. When pivoting end 127A is lowered, clamping end 128A is raised so that the arc shaped notch 132A is moved toward channel wall 124A. This has the effect of narrowing the mouth 125A of channel 122A so that pivot element 126A and channel wall clamp around the rod.

Driving the first fastener 180A into opening 134A and bore 141A allows the first and second locking functions to be performed by a single element, i.e. the first fastener. In addition, the arrangement allows the two locking functions to be performed in a single step. Specifically, the first and second locking functions can be executed during a single continuous rotation of first fastener 180A. The first and second locking functions can be executed simultaneously or at separate times. For example, first fastener 180A can be rotated to lock the connector member 150 to articulation element 130A and simultaneously lock a rod in channel 122A. Alternatively, first fastener 180A can be rotated through a first turn to lock the connector member 150 to articulation element 130A, and then rotated through a second turn to lock a rod in channel 122A, thereby completing the second locking function after completion of the first locking function. The components may also be configured to complete the second locking function before completing the first locking function. The timing of the first and second locking functions can be controlled by the geometry of first fastener 180A, articulation element 130A and pivot element 126A.

Although the present invention has been described in connection with specific embodiments, it should be understood that the invention as claimed should not be unduly limited to such specific embodiments. The specific embodiments described herein are provided only as examples. Various modifications may be made to the devices and methods described herein, including but not limited to various substitutions and combinations of device components and method steps, without departing from the scope of the invention.

For example, the rod to rod connector assembly is primarily described and shown herein as having two identically configured clamping assemblies. The clamping assemblies need not be identically configured, however. For example, the clamping assemblies may have articulating elements with different geometries to provide different ranges of motion. The first clamping assembly may have a generally spherical articulation element to provide polyaxial rotation of its clamping element, while the second clamping assembly may have a cylindrical articulation element that permits monoaxial rotation of its articulation element.

In another variation, the clamping assemblies have polyaxial articulation elements with different shapes that limit the extent to which each clamping body can pivot relative to the connecting member. In such a case, one clamping assembly may be permitted to pivot polyaxially through a larger range of motion relative to the connecting member than the other clamping assembly.

In another variation, the first clamping assembly may have a polyaxial articulation element, while the second clamping assembly has no articulation element. In such a case, the first clamping assembly is permitted to pivot polyaxially relative to the connecting member, while the other clamping assembly is fixed relative to the connecting member. For example, FIG. 4 shows an alternative rod to rod connector assembly 1000 having a first clamping assembly 1100 that is polyaxially connected to a connector member 1500, and a second clamping assembly 1200 fixedly connected to the connector member. First clamping assembly 1100 includes a polyaxial articulation element 1300 that allows the first clamping assembly to move polyaxially with respect to connector element 1500. A first fastener 1120 is configured to lock and unlock polyaxial articulation element 1300. First fastener 1120 is also configured to engage a pivot element 1160 to clamp a rod in first clamping assembly 1100. Second clamping assembly 1200 includes a second fastener 1220 but no articulation element. Second fastener 1220 is configured to engage a pivot element 1260 to clamp a rod in second clamping assembly 1200.

In another variation, the rod to rod connector has a connector member and only one clamping assembly. The clamping assembly connects to a first rod, and the connector member has built-in means for clamping to a second rod. The built-in means for clamping to the second rod may be any known rod clamping mechanism.

In another variation, the connecting member need not have first and second connector member sections that rotate relative to one another. Instead, the connecting member may be a one-piece or "monolithic" component, such as a cross bar, rod or beam. Examples of connecting members that can be used include connecting members shown in U.S. Pat. No. 7,628,799 and U.S. Pat. No. 7,744,632, the contents of which are incorporated by reference in their entireties and for all purposes.

Accordingly, it is intended that the appended claims cover all such variations of the devices, components and methods described herein.

What is claimed:

1. A rod to rod connector comprising:
   a clamping assembly comprising:
      a clamping body having a channel defined by a channel wall for receiving a first spinal rod, and a bore extending through the clamping body;
      a polyaxial articulation element having a hollow body and an opening, the opening being adjacent to the bore extending through the clamping body; and
      a pivot element pivotally connected to the clamping body by a pin on which a first end of the pivot element is mounted, the pivot element configured to clamp a spinal rod between a second end of the pivot element and the channel wall in the clamping assembly, wherein the second end of the pivot element opposes the first end of the pivot element; and
   a connector member for connecting the clamping assembly to a second spinal rod, the connector member comprising a socket having an axis, the socket configured to receive the articulation element of the clamping assembly, with the articulation element polyaxially rotatable relative to the axis of the socket.

2. The rod to rod connector of claim 1, wherein the connector member comprises a first connector member section and a second connector member section configured to be pivotally coupled with the first connector member section.

3. The rod to rod connector of claim 2, wherein the first connector member section comprises a plate forming a first slot, and the second connector member section comprises a plate forming a second slot.

4. The rod to rod connector of claim 3, comprising a connector element extending through the first and second slots and pivotally connecting the first and second connector member sections.

5. The rod to rod connector of claim 1, comprising a fastener extending through the socket in the connector member, and through the opening and bore in the clamping assembly, the fastener interconnecting the connector member and clamping assembly.

6. The rod to rod connector of claim 5, wherein the articulation element of the clamping assembly comprises a plurality of wall sections separated from one another by slits, each wall section being displaceable between a first position, in which each wall section is in a relaxed state, and a second position, in which each wall section is displaced radially outwardly from the first position.

7. The rod to rod connector of claim 6, wherein the fastener is drivable into the opening of the clamping assembly to displace the wall sections of the articulation element from the first position to the second position.

8. The rod to rod connector of claim 7, wherein the first end of the pivot element of the clamping assembly and defines a pivot end and the second end of the pivot element defines a clamping end, the pivot end being aligned with the bore in the clamping assembly and positioned to be engaged by the fastener when the fastener is driven through the opening of the clamping assembly.

9. The rod to rod connector of claim 8, wherein the fastener is operable to lock the connector member relative to the articulation element and clamp a first spinal rod in the channel of the clamping assembly in a single rotation step.

10. A rod to rod connector comprising:
a first clamping assembly comprising:
   a clamping body having a channel defined by a channel wall for receiving a first spinal rod, and a bore extending through the clamping body;
   a polyaxial articulation element having a hollow body and an opening, the opening being adjacent to the bore extending through the clamping body; and
   a first pivot element pivotally connected to the clamping body by a first pin on which a first end of the first pivot element is mounted, the first pivot element configured to clamp a first spinal rod between a second end of the first pivot element and the channel wall in the first clamping assembly, wherein the second end of the first pivot element opposes the first end of the first pivot element;
a second clamping assembly comprising:
   a clamping body having a channel defined by a channel wall for receiving a second spinal rod, and a bore extending through the clamping body;
   a polyaxial articulation element having a hollow body and an opening, the opening being adjacent to the bore extending through the clamping body; and
   a second pivot element pivotally connected to the clamping body, the second pivot element configured to clamp a second spinal rod between the second pivot element and the channel wall in the second clamping assembly; and
a connector member for connecting the first clamping assembly with the second clamping assembly, the connector member comprising a first socket having a first axis, and a second socket having a second axis,
the first socket configured to receive the articulation element of the first clamping assembly, and the second socket configured to receive the articulation element of the second clamping assembly, with the articulation element of the first clamping assembly polyaxially rotatable relative to the first axis and the articulation element of the second clamping assembly polyaxially rotatable relative to the second axis.

11. The rod to rod connector of claim 10, wherein the connector member comprises a first connector member section and a second connector member section configured to be pivotally coupled with the first connector member section.

12. The rod to rod connector of claim 11, wherein the first connector member section comprises a link portion forming a first slot, and the second connector member section comprises a link portion with a second slot.

13. The rod to rod connector of claim 12, comprising a connector element extending through the first and second slots and pivotally connecting the first and second connector member sections.

14. The rod to rod connector of claim 10, comprising a first fastener extending through the first socket in the connector member, and through the opening and bore in the first clamping assembly, the first fastener interconnecting the connector member and first clamping assembly.

15. The rod to rod connector of claim 14, wherein the articulation element of the first clamping assembly comprises a plurality of wall sections separated from one another by slits, each wall section being displaceable between a first position, in which each wall section is in a relaxed state, and a second position, in which each wall section is displaced radially outwardly from the first position.

16. The rod to rod connector of claim 15, wherein the first fastener is drivable into the opening of the first clamping assembly to displace the wall sections of the articulation element to the second position.

17. The rod to rod connector of claim 16, wherein the first end of the first pivot element of the first clamping assembly defines a pivot end and the second end of the first pivot element defines a clamping end, the pivot end being aligned with the bore in the first clamping assembly and positioned to be engaged by the first fastener when the first fastener is driven through the bore of the first clamping assembly.

18. The rod to rod connector of claim 17, wherein the first fastener is operable to lock the connector member relative to the articulation element and clamp a first spinal rod in the channel of the first clamping assembly in a single rotation step.

19. A rod to rod connector comprising:
a clamping assembly comprising:
   a clamping body having a channel defined by a channel wall for receiving a first spinal rod, and a bore extending through the clamping body;
   a polyaxial articulation element having a hollow body and an opening, the opening being adjacent to the bore extending through the clamping body; and
   a pivot element pivotally connected to the clamping body, the pivot element configured to clamp a spinal rod between the pivot element and the channel wall in the clamping assembly, wherein the pivot element comprises a clamping end and a pivot end, the pivot end aligned with the bore in the clamping assembly and positioned to be engaged by the fastener when the fastener is driven through the opening of the clamping assembly; and
a connector member for connecting the clamping assembly to a second spinal rod, the connector member comprising a socket having an axis, the socket configured to receive the articulation element of the clamping assembly, with the articulation element polyaxially rotatable relative to the axis of the socket.

20. The rod to rod connector of claim 19, wherein the connector member comprises a first connector member section and a second connector member section configured to be pivotally coupled with the first connector member section.

21. The rod to rod connector of claim 20, wherein the first connector member section comprises a plate forming a first slot, and the second connector member section comprises a plate forming a second slot.

22. The rod to rod connector of claim 21, comprising a connector element extending through the first and second slots and pivotally connecting the first and second connector member sections.

23. The rod to rod connector of claim 19, comprising a fastener extending through the socket in the connector member, and through the opening and bore in the clamping assembly, the fastener interconnecting the connector member and clamping assembly.

24. The rod to rod connector of claim 23, wherein the articulation element of the clamping assembly comprises a plurality of wall sections separated from one another by slits, each wall section being displaceable between a first position, in which each wall section is in a relaxed state, and a second position, in which each wall section is displaced radially outwardly from the first position.

25. The rod to rod connector of claim 24, wherein the fastener is drivable into the opening of the clamping assembly to displace the wall sections of the articulation element from the first position to the second position.

26. The rod to rod connector of claim 23, wherein the fastener is operable to lock the connector member relative to the articulation element and clamp a first spinal rod in the channel of the clamping assembly in a single rotation step.

27. A rod to rod connector comprising:
a first clamping assembly comprising:
   a clamping body having a channel defined by a channel wall for receiving a first spinal rod, and a bore extending through the clamping body;
   a polyaxial articulation element having a hollow body and an opening, the opening being adjacent to the bore extending through the clamping body; and
   a pivot element pivotally connected to the clamping body, the pivot element configured to clamp a first spinal rod between the pivot element and the channel wall in the first clamping assembly, wherein the pivot element of the first clamping assembly comprises a clamping end and a pivot end, the pivot end aligned with the bore in the first clamping assembly and positioned to be engaged by the first fastener when the first fastener is driven through the bore of the first clamping assembly;
a second clamping assembly comprising:
   a clamping body having a channel defined by a channel wall for receiving a second spinal rod, and a bore extending through the clamping body;
   a polyaxial articulation element having a hollow body and an opening, the opening being adjacent to the bore extending through the clamping body; and
   a pivot element pivotally connected to the clamping body, the pivot element configured to clamp a second spinal rod between the pivot element and the channel wall in the second clamping assembly; and
a connector member for connecting the first clamping assembly with the second clamping assembly, the connector member comprising a first socket having a first axis, and a second socket having a second axis,
the first socket configured to receive the articulation element of the first clamping assembly, and the second socket configured to receive the articulation element of the second clamping assembly, with the articulation element of the first clamping assembly polyaxially rotatable relative to the first axis and the articulation element of the second clamping assembly polyaxially rotatable relative to the second axis.

28. The rod to rod connector of claim 27, wherein the connector member comprises a first connector member section and a second connector member section configured to be pivotally coupled with the first connector member section.

29. The rod to rod connector of claim 28, wherein the first connector member section comprises a link portion forming a first slot, and the second connector member section comprises a link portion with a second slot.

30. The rod to rod connector of claim 29, comprising a connector element extending through the first and second slots and pivotally connecting the first and second connector member sections.

31. The rod to rod connector of claim 27, comprising a first fastener extending through the first socket in the connector member, and through the opening and bore in the first clamping assembly, the first fastener interconnecting the connector member and first clamping assembly.

32. The rod to rod connector of claim 31, wherein the articulation element of the first clamping assembly comprises a plurality of wall sections separated from one another by slits, each wall section being displaceable between a first position, in which each wall section is in a relaxed state, and a second position, in which each wall section is displaced radially outwardly from the first position.

33. The rod to rod connector of claim 32, wherein the first fastener is drivable into the opening of the first clamping assembly to displace the wall sections of the articulation element to the second position.

34. The rod to rod connector of claim 31, wherein the first fastener is operable to lock the connector member relative to the articulation element and clamp a first spinal rod in the channel of the first clamping assembly in a single rotation step.

35. A rod to rod connector comprising:
a clamping assembly comprising:
   a clamping body having a channel defined by a channel wall for receiving a first spinal rod, and a bore extending through the clamping body;
   a polyaxial articulation element having a hollow body and an opening, the opening being adjacent to the bore extending through the clamping body; and
   a pivot element pivotally connected to the clamping body, the pivot element configured to clamp a spinal rod between the pivot element and the channel wall in the clamping assembly;
a connector member for connecting the clamping assembly to a second spinal rod, the connector member comprising a socket having an axis, the socket configured to receive the articulation element of the clamping assembly, with the articulation element polyaxially rotatable relative to the axis of the socket; and
a fastener extending through the socket in the connector member, and through the opening and bore in the clamping assembly, the fastener interconnecting the connector member and clamping assembly, wherein the fastener is operable to lock the connector member relative to the articulation element and clamp a first spinal rod in the channel of the clamping assembly in a single rotation step.

36. The rod to rod connector of claim 35, wherein the connector member comprises a first connector member section and a second connector member section configured to be pivotally coupled with the first connector member section.

37. The rod to rod connector of claim 36, wherein the first connector member section comprises a plate forming a first slot, and the second connector member section comprises a plate forming a second slot.

38. The rod to rod connector of claim 35, comprising a connector element extending through the first and second slots and pivotally connecting the first and second connector member sections.

39. The rod to rod connector of claim 35, wherein the articulation element of the clamping assembly comprises a plurality of wall sections separated from one another by slits, each wall section being displaceable between a first position, in which each wall section is in a relaxed state, and a second position, in which each wall section is displaced radially outwardly from the first position.

40. The rod to rod connector of claim 35, wherein the fastener is drivable into the opening of the clamping assembly to displace the wall sections of the articulation element from the first position to the second position.

41. A rod to rod connector comprising:
   a first clamping assembly comprising:
      a clamping body having a channel defined by a channel wall for receiving a first spinal rod, and a bore extending through the clamping body;
      a polyaxial articulation element having a hollow body and an opening, the opening being adjacent to the bore extending through the clamping body;
      a pivot element pivotally connected to the clamping body, the pivot element configured to clamp a first spinal rod between the pivot element and the channel wall in the first clamping assembly; and
      a first fastener extending through the first socket in the connector member, and through the opening and bore in the first clamping assembly, the first fastener interconnecting the connector member and first clamping assembly, wherein the first fastener is operable to lock the connector member relative to the articulation element and clamp a first spinal rod in the channel of the first clamping assembly in a single rotation step;
   a second clamping assembly comprising:
      a clamping body having a channel defined by a channel wall for receiving a second spinal rod, and a bore extending through the clamping body;
      a polyaxial articulation element having a hollow body and an opening, the opening being adjacent to the bore extending through the clamping body; and
      a pivot element pivotally connected to the clamping body, the pivot element configured to clamp a second spinal rod between the pivot element and the channel wall in the second clamping assembly; and
   a connector member for connecting the first clamping assembly with the second clamping assembly, the connector member comprising a first socket having a first axis, and a second socket having a second axis,
   the first socket configured to receive the articulation element of the first clamping assembly, and the second socket configured to receive the articulation element of the second clamping assembly, with the articulation element of the first clamping assembly polyaxially rotatable relative to the first axis and the articulation element of the second clamping assembly polyaxially rotatable relative to the second axis.

42. The rod to rod connector of claim 41, wherein the connector member comprises a first connector member section and a second connector member section configured to be pivotally coupled with the first connector member section.

43. The rod to rod connector of claim 42, wherein the first connector member section comprises a link portion forming a first slot, and the second connector member section comprises a link portion with a second slot.

44. The rod to rod connector of claim 43, comprising a connector element extending through the first and second slots and pivotally connecting the first and second connector member sections.

45. The rod to rod connector of claim 41, wherein the articulation element of the first clamping assembly comprises a plurality of wall sections separated from one another by slits, each wall section being displaceable between a first position, in which each wall section is in a relaxed state, and a second position, in which each wall section is displaced radially outwardly from the first position.

46. The rod to rod connector of claim 41, wherein the first fastener is drivable into the opening of the first clamping assembly to displace the wall sections of the articulation element to the second position.

* * * * *